| United States Patent [19] | [11] Patent Number: 5,021,592 |
| Beer et al. | [45] Date of Patent: Jun. 4, 1991 |

[54] REDOX-ACTIVE CENTRES

[75] Inventors: Paul D. Beer; Elizabeth L. Tite, both of Birmingham, England

[73] Assignee: Imperial Chemical Industries PLC, London, England

[21] Appl. No.: 343,342

[22] Filed: Apr. 26, 1989

[30] Foreign Application Priority Data

Apr. 26, 1988 [GB] United Kingdom ............... 8809862
Oct. 5, 1988 [GB] United Kingdom ............... 8823384

[51] Int. Cl.$^5$ ...................... C07C 15/02; C07C 11/00; C07C 15/00
[52] U.S. Cl. ........................................ 556/1; 556/136; 556/138; 556/140
[58] Field of Search .................. 556/1, 136, 137, 138, 556/140, 42

[56] References Cited

U.S. PATENT DOCUMENTS 3,644,455  2/1972  Onsager .......................... 556/138
4,767,873  8/1988  Katz et al. ......................... 556/42
4,888,032  12/1989  Busch ........................... 556/138 X

*Primary Examiner*—Arthur C. Prescott
*Attorney, Agent, or Firm*—Cushman, Darby & Cushman

[57] ABSTRACT

A polymetallocene macrocycle which comprises a ring of alternating in-chain aromatic residues and in-chain alkylene units and which bears four or more transition metal complexes or metallocenyl groups. Such macrocycles are redox-active hydrophobic host molecules potentially useful as electron transfer mediators, for chemical sensor design, as redox catalysts or as Second Harmonic Generator material.

8 Claims, No Drawings

REDOX-ACTIVE CENTRES

This invention relates to macrocyclic products, particularly macrocyclic products derived from metallocenes, more particularly where the metallocene is ferrocene and to a process for the preparation thereof.

The design and synthesis of receptor molecules containing a redox-active centre in close proximity to a crown-ether or cryptand coordination site are known. It has now been recognised by the inventors that it would be desirable to incorporate redox centres into hydrophobic host molecules to produce a product which would allow (i) interactions between the redox-active moiety and an included organic substrate to be detected and (ii) potential catalytic interactions to be investigated.

We have now prepared redox-active hydrophobic host molecules comprising a ring of alternating in-chain aromatic residues and in-chain alkylene units which ring bears four or more transition metal complexes or so-called metallocenyl groups.

According to the present invention there is provided a polymetallocene macrocycle of the General Formula I

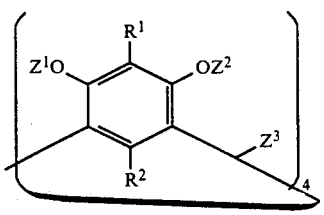

wherein $Z^1$ and $Z^2$, which may be the same as or diffferent from each other, may be hydrogen, hydrocarbyl, acyl, aroyl, alkylimino, acylimino, metallocene-CO—, or metallocene-CH$_2$—, or $Z^1$ and $Z^2$, on one aromatic group may together form a link between the 0's thereof or a $Z^1$ on one aromatic group and $Z^2$ on an adjacent aromatic group may form an intramolecular link $R^1$ and $R^2$, which may be the same as or different from each other, may be hydrogen, hydrocarbyl, acyl, aroyl, nitro, amino, hydroxyl, carbonyl, carboxyl, etc or $R^2$ may be ferrocenecarbonyloxy ; and $Z^3$ is a hydrocarbyl group, a heterocyclic group, a metallocene residue or a transition metal complex of the heterocyclic group; except that at least one of $Z^1$, $Z^2$, or $Z^3$ bears a metallocene residue and/or $Z^3$ is a complex of a heterocyclic group wherein the metal in $Z^1$, $Z^2$ or $Z^3$ is a transition metal.

In the General Formula I, $Z^1$ and $Z^2$ are preferably acyl groups or metallocene carbonyl residues. Where $Z^1$ and $Z^2$ are acyl groups, preferably they are aroyl groups, more preferably benzoyl to give a product with preferable solubility.

In the General Formula I, where $R^1$ is not hydrogen, $R^2$, preferably is hydrogen for steric considerations.

The metallocene residue present in General Formula I, is preferably derived from a five membered ring of the General Formula II

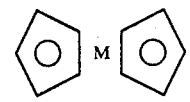

where M is a transition meta 1. However, we do not exlcude the possibility that is could be derived from one or more rings of different sizes, e.g. six- or seven-membered rings, such that the metallocene residues present in compounds of the General Formula I may have a structure represented by, for example, General Formulae III a, b, c,

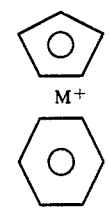

IIIa

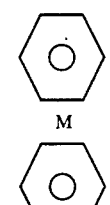

IIIb

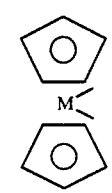

IIIc

Where M has the meaning hereinbefore ascribed to it.

Where the aforementioned metallocene residue bears a positive charge, e.g. as in General Formula IIIa, the anion associated therewith will be readily chosen by the man skilled in the art; typically it is a halide or PF$_6$—.

In the General Formula I, where $Z^3$ is a hydrocarbyl group it is preferably an alkyl group having at least five C atoms to improve solubility. We have found that such a group tends to improve the solubility of the polymetallocene macrocycle, although we do not exclude the possibility that it may be an alternative hydrocarbyl, for example an aryl group, e.g. phenyl.

As examples of the heterocyclic group $Z^3$ in the General Formula I, where $Z^3$ is a heterocyclic group, may be mentioned inter alia cyclic ethers, e.g.

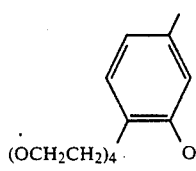

or, a pyridyl or a bipyrdidyl, e.g.,

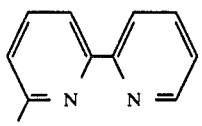

residue.

It will be appreciated that where $Z^3$ is a certain heterocyclic group, e.g. a pyridyl, or particularly the aforementioned bipyridyl, the compound of General Formula I may be reacted with a transition metal complex such that $Z^3$ is converted into a metal-containing residue, e.g.

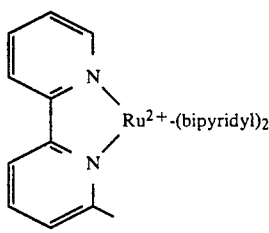

IV

Furthermore, where $Z^1$ and/or $Z^2$ in a compound of General Formula I is a metallocene residue bearing a first metal, e.g.

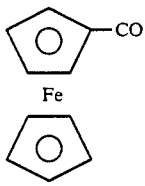

and $Z^3$ is a second metal-containing residue, e.g. of General Formula IV, it will be appreciated that compounds of the General Formula I may provide different redox-active centres at $Z^1/Z^2$ from $Z^3$.

As examples of the transition metal M from which the metallocene derivative is derived, where $Z^1$, $Z^2$ or $Z^3$ is a metallocene residue in compounds of General Formula I or the metal complex is derived, where $Z^3$ is a transition metal complex of a heterocyclic compound in compounds of the General Formula I, may be mentioned inter alia Mo, W or preferably a metal of Group VIII of the Periodic Table, particularly preferably ruthenium, cobalt or iron or more particularly preferably iron.

It will be appreciated that the presence of a substituent at the position ortho to both the $OZ^1$ and $OZ^2$ groups on an aromatic ring in General Formula I may well hinder or prevent the formation of an intramolecular link between those groups.

According to a further aspect of the present invention there is provided a process for the preparation of a polymetallocene macrocycle which process comprises at least the steps of:

A. reacting a resorcinol with a carboxaldehyde;
B. reacting the product of step A with
   (i) a carboxylic acid, or a suitable derivative thereof, under conditions such that substantially all of the hydroxyl groups in the product from Step A are converted into ester groups; or
   (ii) with an ether-forming halo-derivative under conditions such that substantially all of the hydroxyl groups in the product from Step A are converted into ether groups;

with the proviso that a metallocene derivative is used in at least one of the said steps, preferably in Step A.

It will be appreciated that the resorcinol used therein will have at least both the 2- and 4-positions unsubstituted. The resorcinol may bear a substituent, eg an alkyl, aryl, hydroxyl, carboxyl or nitro group, on the carbon atom ortho to both hydroxyl groups, ie $R^1$, which does not unduly inhibit the process of the present invention. However, where $R^2$ is not hydrogen, $R^1$ preferably is hydrogen.

The metallocenecarboxaldehyde used in Step A of the process according to the present invention may be prepared by methods known in the art, e.g. K Schögl, Monatsch. Chem., 1957, 88, 60.

Step A in the process of the present invention is preferably carried out in a polar organic solvent, more preferably ethanol, in the presence of a suitable acidic catalyst, preferably hydrochloric acid, e.g. about 10M HCl. The product of Step A, where ferrocene carboxaldehyde is the metallocene carboxaldehyde which is reacted with resorcinol, has the structure represented by General Formula V

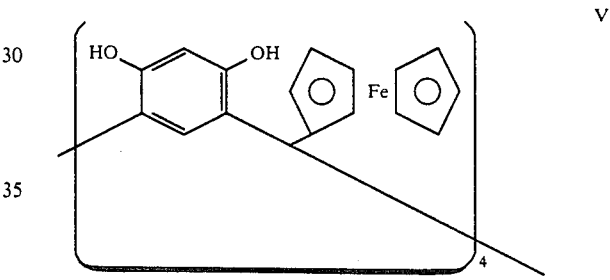

V

In Step B of the process according to the present invention, the product of Step A, ie a compound of the General Formula I wherein $Z^1$ and $Z^2$ are hydrogen, e.g. V, is preferably reacted with an acid chloride, although we do not exclude the possibility that an alternative ester-forming acid derivative, e.g. an anhydride, may be used.

Preferably the product of Step A is benzoylated such that a product of desired solubility is obtained, or treated with a metallocene carbonyl chloride, e.g. ferrocenecarbonyl chloride to afford a novel product of desired solubility. Step B is preferably carried out in suspension in a suitable liquid, e.g. tetrahydrofuran. Where ferrocenecarbonyl chloride and a product of the General Formula V are used in Step B the product has the structure shown in General Formula VI

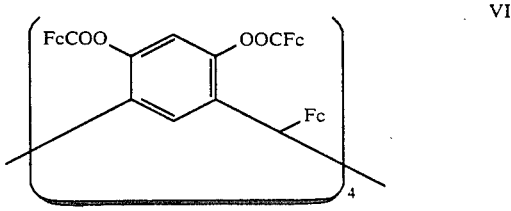

VI

-continued (where Fc represents ferrocence).

Where a 1,1-bis (chlorocarbonyl)-Ferrococene and a product of the General Formula V are used in Step B a product of General Formula VII is obtained.

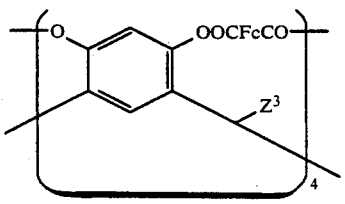

VII

Wherein $Z^3$ is Fc

As examples of ether-forming halo-derivatives which may be reacted in Step B with the product from Step A may be mentioned inter alia aralkyl halides, e.g. benzyl bromide, metallocenyl halides, and alkylene dihalides, e.g. bromochloromethane. The preparation of an ether according to the present invention may be effected by reacting the aforesaid halo-derivatives with a compound of the General Formula I, where $Z^1$ and $Z^2$ represent hydrogen, under conditions known in the art, e.g. using sodium carbonate as catalyst.

Where an ether forming dihaloalkane is used in Step B the product often has the structure shown in General Formula VIII.

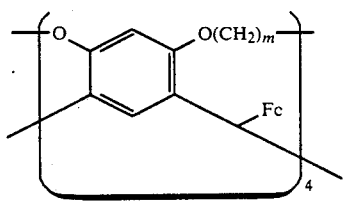

VIII wherein m is typically 1–6 and preferably 1.

The macrocyclic compound according to the present invention comprises a transition metal it may be used as an electron transfer mediator, for chemical sensor design, as a redox catalyst or as a Second Harmonic Generator (SHG) material.

The present invention is further illustrated by reference to the following Examples.

EXAMPLE 1

This Example illustrates a compound according to the present invention, containing four redox-active centres.

Concentrated hydrochloric acid (6 ml) was rapidly added to a homogeneous solution of resorcinol (3.19 g, 29 mmol) and ferrocenecarboxaldehyde (6.19 g, 29 mmol) in ethanol (30 ml). The reaction mixture was stirred at about 75° C. for 4 hours and then cooled to 0° C. The compound having the General Formula V formed as a black precipitate; it was filtered off and washed with water until the washings were no longer acidic. The black precipitate was dried in vacuo.

The black precipitate was insoluble in substantialy all common solvents including base. It was too involatile for analysis by mass spectrometry. The infra-red spectrum revealed a large hydrogen-bonding peak between 3700 and 2700cm$^{-1}$. It had a melting point above 250° C.

EXAMPLE 2

This Example illustrates a compound according to the present invention, wherein the aromatic rings bear ester groups.

Triethylamine (2 ml) and then an excess of benzoyl chloride (2.8 g) were added to a suspension of the black precipitate, prepared in Example 1 in dried tetrahydrofuran. The resulting mixture was refluxed for four days, cooled, evaporated to dryness, washed with base and water and the product thereform was purified by column chromatography down an alumina column with diethyl ether/dichloromethane in ratio 75:25 as the eluent. The compound of General Formula I (wherein both $Z^1$ and $Z^2$ represent PhCO, $R^1$ and $R^2$ represent hydrogen and $Z^3$ represents ferrocene) was obtained as orange crystals.

Analysis of the orange crystals revealed the following data:

$^1$H nmr (CDCl$_3$) signals at: 3.93 (24H,s) 4.05 (4H,s), 4.12 (4H,s), 4.23 (4H,s), 5.65 (4H,s), 6.64 (2H,s), 6.73 (2H,s), 6.75 (2H,s) 7.20, 7.25 (8H,m), 7.42–7.58 (16H,m), 7.8–7.99 (16H,m).

$^{13}$C nmr (CDCl$_3$) signals at: 164.70, 163.30, 14 7 17, 145.57, 133.90, 133.14, 131.15, 130.35, 129.88, 128.24, 116.47, 114.82, 89.94, 77.21, 76.90, 76.58, 69.06, 68.51, 67.98, 67.09 32.20.

The infra-red spectrum (KBr disc) of the orange crystals had a peak at 1735 cm$^{-1}$ (C=O). Mass spectroscopy of the orange crystals indicated M/Z=2057 and they were found to have a melting point above 250° C. (decomposition).

Electrochemical experiments (acetonitrile, SCE) revealed two, two electron reversible oxidation waves at +0.575 v and +0.665 v corresponding to the oxidation of the respective four ferrocenyl moieties.

EXAMPLE 3

This Example illustrates a further compound according to the present invention, containing twelve redox-active centres.

The procedure of Example 2 was repeated except that an excess of ferrocenecarbonyl chloride was used instead of benzoyl chloride.

The ferrocenecarbonyl chloride was prepared by the process described by Falk, Krasa and Schlogel in Monatschefte für Chemie, 1969, 100, 152.

The structure of the product was confirmed as that of a compound of General Formula VI by the following analysis which revealed the following data: $^1$H nmr (CDCl$_3$): signals at 4.06, 4.19, 4.38, 4.82 (108H, 4×s), 5.48 (4H,s), 6.72 (4H,s) and 7.26 (CHCl$_3$); infra-red (KBr disc): peak at 1720 cm$^{-1}$ (C=O); mass spectroscopy: M/Z 2921; and melting point above 250° C.

EXAMPLE 4

This Example illustrates a further compound according to the present invention wherein there are intramolecular alkylene bridges.

A portion (6.12 gms, 5 mmol) of the di-hydroxy compound prepared in Example 1, anhydrous potassium carbonate (8 gms, 58 mmol) and bromochloromethane (4 gms, 31 mmol) in dried dimethylformamide (150 mls) were stirred at about 85° C. in a nitrogen atmosphere for 68 hours. The solvent was evaporated under reduced pressure and the brown residue was triturated with dichloromethane. The mixture was filtered through a bed of Celite, the eluate was dried over magnesium sulphate and evaporated at reduced pressure. The residual brown solid was chromatographed on an alumina column with $CH_2Cl_2$ as the eluent. Slow evaporation of the eluent gave orange crystals (0.08 g, 1% yield) of the General Formula VIII wherein m is 1.

Analysis of the product gave the following data: $^1H$ nmr ($CDCl_3$) signals at: 3.75 (20H,s), 4.28 (8H,s), 4.42 (8H,s), 4.50, 4.53 (4H, 2×s), 5.30 ($CH_2Cl_2$), 5.83, 5.86 (4H, 2×s). 5.96 (8H,s) 6.55 (4H,s), 7.26 ($CHCl_3$) and 7.64 (4H,s);

$^{13}C$ nmr ($CDCl_3$) signals at 38.87, 68.32, 68.19, 70.49, 75.60, 76.35, 77.00, 78.43, 79.57, 87.88, 99.69, 115.89, 125.09, 138.87 and 153.86; Mass spectroscopy: M/Z 1272; and melting point above 250° C.

EXAMPLE 5

This Example illustrates a yet further compound according to the present invention, bearing eight ferrocene residues.

First Stage

Concentrated hydrochloric acid (10 mls) was added dropwise to a stirred solution of resorcinol (11 g, 0.1 mol) and acetaldehyde (4.41 g, 0.1 mol) in distilled water (40 mls). A cream precipitate rapidly formed. The reaction mixture was stirred at 75° C. for one hour, then cooled in a freezer. The cream precipitate was then filtered off, washed with water until the washings were no longer acidic, and dried under vacuum.

Second Stage

Ferrocene carbonyl chloride (0.74 g, $3 \times 10^{-3}$ mol; prepared as described in Example 3), triethylamine (0.6 mls, $4 \times 10^{-3}$ mols) and dimethylamino pyridine (catalytic amount, 0.03 g) were stirred under nitrogen at room temperature in dried tetrahydrofuran (75 mls). A portion (0.081 g, $1.5 \times 10^{-4}$ mols) of the product from the first stage in dried tetrahydrofuran (75 mls) was added to the above reaction mixture. It was heated at reflux for 2 hours and then rotary evaporated. The residue from the rotary evaporator was dissolved in dichloromethane. This solution was washed with water, and the organic layer was dried with magnesium sulphate. The product was purified by column chromatography down an alumina column. The material eluted with dichloromethane was discarded, and the material eluted with dichloromethane/methanol (99 75:0.25% v/v) was collected and recrystallised from dichloromethane/methanol to yield orange crystals (overall yield 33%) of the General Formula I wherein $Z^1=Z^3=$ferrocenecarbonyl and $Z^3$ is methyl. following properties; Nuclear magnetic resonance revealed signals at $^1H$ nmr ($CDCl_3$) (16H,s), 4.62, 4.64, 4.66, 4.68 (4H,q); 4.71 (4H,s), 4.76 (4H,s), 4.83 (4H,s), 4.94 (4H,s) 5.29 ($CH_2Cl_2$), 6.34 (2H,s), 7.06 (2H,s), 7.14 (2H,s) 7.25 ($CHCl_3$), 7.65 (2H,s); and Nuclear magnetic resonance revealed signals at: $^{13}C$ nmr ($CDCl_3$): 20.58, 69.83, 70.39, 71.58, 71.65, 76.58, 76.76, 78.81, 76.90, 77.10, 77.22, 115 56, 116.41, 125.87, 132.51, 135.83, 145.88, 147.89, 169.18, 169.68, 207.09;

The infra-red spectrum (KBr disc) had a peak at 1730 $cm^{-1}$ (C=0). Mass spectroscopy revealed, M/Z=2241 and it was found to have a melting point greater than 250° C. (decomposition).

EXAMPLE 6

This Example illustrates a yet further compound according to the invention wherein there are intramolecular metallocene bridges.

A portion of the dihydroxy compound prepared from the reaction of resorcinol and acetaldehyde by the method of Hogberg (Journal of Organic Chemistry, 1980, Vol 45, 4498) i.e. a compound of the General Formula I wherein $Z^1=Z^2=H$ and $Z^3=CH_3$) was treated with an excess of 1,1'-bis-chlorocarbonyl-ferrocene (prepared by the method of Lorkowski, Pannier and Wende, J Prakt. Chem. 1967, 35,149) under the conditions described in Example 2.

The product was obtained as an orange crystalline solid. The structure thereof was confirmed by chemical analysis, mass spectrometry and $^1H$ and $^{13}C$ nmr spectroscopy, as an intra-molecular bridged compound of General Formula VII wherein $Z^3$ is $CH_3$.

We claim:

1. A polymetallocene macrocycle of the General Formula

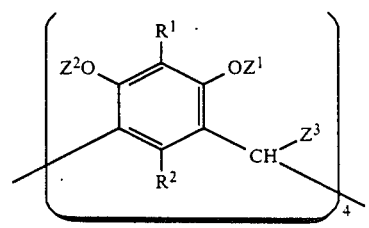

wherein $Z^1$ and $^2$, which may be in the same as or different from each other, may be hydrogen, hydrocarbyl, acyl, aroyl, alkylimino, acylimino, metallocene-CO— or metallocene-$CH_2$—, or $Z^1$ and $Z^2$ on one aromatic group may together form a link between the 0's thereof or $Z^1$ on one aromatic group and $Z^2$ on an adjacent aromatic group may form an intramolecular link between the 0's on the two said groups;

$R^1$ and $R^2$, which may be the same as or different from each other, may be hydrogen, hydrocarbyl, acyl, aroyl, nitro, amino, hydroxyl, carbonyl, carboxyl, etc or $R^2$ may be ferrocenecarbonyloxy; and $Z^3$ is a hydrocarbyl group, a metallocene residue, or a heterocyclic group or a transition metal complex thereof except that least one of $Z^1$, $Z^2$ or $Z^3$ bears a metallocene residue and/or $Z^3$ is a metal complex of the heterocyclic group wherein the metal in $Z^1$, $Z^2$, or $Z^3$ is a transition metal.

2. A polymetallocene macrocyle as claimed in claim 1 wherein the metallocene residue is derived from a five-membered ring of the general formula

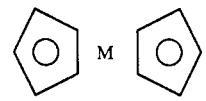

wherein M is a transition metal.

3. A polymetallocene macrocycle as claimed in claim 1 wherein the transition metal is iron.

4. A polymetallocene macrocycle as claimed in claim 1 wherein $Z^3$ is a metallocene residue.

5. A polymetallocene macrocycle as claimed in claim 1, wherein $Z^1$ and $Z^2$ separately represent metallocene residues.

6. A polymetallocene macrocycle as claimed in claim 1 wherein $Z^1$ and $Z^2$ on adjacent resorcinol residues together provide a bridge between oxygen atoms on the two resorcinol residues.

7. A polymetallocene macrocycle as claimed in claim 6 wherein the bridge comprises an alkylene unit and $Z^3$ is a metallocene residue.

8. A polymetallocene macrocycle as claimed in claim 6 wherein the bridge comprises a metallocene residue and $Z^3$ is a hydrocarbyl group.

* * * * *